United States Patent
Wu et al.

(10) Patent No.: US 8,940,235 B2
(45) Date of Patent: Jan. 27, 2015

(54) THIN-FILM TRANSISTORS FOR CHEMICAL SENSOR APPLICATIONS

(75) Inventors: Yiliang Wu, Oakville (CA); Ping Liu, Mississauga (CA); Anthony James Wigglesworth, Oakville (CA)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 224 days.

(21) Appl. No.: 13/252,332

(22) Filed: Oct. 4, 2011

(65) Prior Publication Data

US 2013/0084644 A1 Apr. 4, 2013

(51) Int. Cl.
| | | |
|---|---|---|
| G01N 27/00 | (2006.01) | |
| G01N 27/414 | (2006.01) | |
| H01L 51/00 | (2006.01) | |
| H01L 51/05 | (2006.01) | |

(52) U.S. Cl.
CPC ........ *G01N 27/4146* (2013.01); *H01L 51/0036* (2013.01); *H01L 51/0048* (2013.01); *H01L 51/0558* (2013.01)
USPC ............ 422/82.01; 422/98; 436/149; 257/40; 257/E51.006

(58) Field of Classification Search
None
See application file for complete search history.

(56) References Cited

U.S. PATENT DOCUMENTS

| | | |
|---|---|---|
| 2008/0274912 A1 | 11/2008 | Johnson et al. |
| 2010/0176837 A1 | 7/2010 | Kummel et al. |
| 2010/0325073 A1 | 12/2010 | Haick |

OTHER PUBLICATIONS

Hsieh, G-W. et al. High performance nanocomposite thin film transistors with bilayer carbon nanotube-polythionphene active channel by ink-jet printing, 2009, JOurnal of Applied Physics, vol. 106, pp. 123706-1 to 123706-7.*
Wang, F. et al. Carbon nanotube/polythiophene chemiresistive sensors for chemical warfare agents, 2008, Journal of American chemical society, vol. 130, pp. 5392-5393.*
Liao, F.J. Polythiophene transistors as gas sensors ofr electronic nose sensors, 2009, Doctor dissertation, university of California, Berkley.*
Penza, M. et al. Surface modification of carbon nanotube networked films without Au nanoclusters for enhanced NO2 gas sensing applications, 2008, Journal of Sensors, vol. 2008, pp. 1-8.*
U.S. Appl. No. 13/011,130, filed Jan. 21, 2011, entitled "Electronic Device", by Yiliang Wu et al.
U.S. Appl. No. 13/011,139, filed Jan. 21, 2011, entitlted "Semiconductor Composition", by Yiliang Wu.

* cited by examiner

*Primary Examiner* — Robert Xu
(74) *Attorney, Agent, or Firm* — Harness, Dickey & Pierce, P.L.C.

(57) ABSTRACT

A chemical sensor is disclosed. The chemical sensor is an electronic device including in specific embodiments a first transistor and a second transistor. The first transistor includes a semiconducting layer made of a first semiconductor and carbon nanotubes. The second transistor includes a semiconducting layer made of a second semiconductor, and does not contain carbon nanotubes. The two transistors vary in their response to chemical compounds, and the differing response can be used to determine the identity of certain chemical compounds. The chemical sensor can be useful as a disposable sensor for explosive compounds such as trinitrotoluene (TNT). The electronic device is used in conjunction with an analyzer that processes information generated by the electronic device.

6 Claims, 3 Drawing Sheets

THIN-FILM TRANSISTORS FOR CHEMICAL SENSOR APPLICATIONS

BACKGROUND

The present disclosure relates to electronic devices containing chemically sensitive thin-film transistors (TFTs). The devices can contain one or more different types of transistors, and are useful in the detection, identification, and/or quantification of compounds, such as volatile compounds associated with explosive materials.

TFTs are generally composed of, on a substrate, an electrically conductive gate electrode, source and drain electrodes, an electrically insulating gate dielectric layer which separate the gate electrode from the source and drain electrodes, and a semiconducting layer which is in contact with the gate dielectric layer and bridges the source and drain electrodes. Their performance can be determined by the field effect mobility and the current on/off ratio of the overall transistor.

Organic thin-film transistors (OTFTs) can be fabricated using low-cost solution-based patterning and deposition techniques, such as spin coating, solution casting, dip coating, stencil/screen printing, flexography, gravure, offset printing, ink jet-printing, micro-contact printing, and the like. This low cost permits OTFTs to be used in applications where disposal of the electronic device may be useful.

The detection of explosive compounds is desirable in homeland security applications and other protective functions. Explosive compounds typically contain nitrogen and include trinitrotoluene (TNT), cyclotrimethylenetrinitramine (RDX), and pentaerythritol tetranitrate (PETN). Some chemical warfare agents also contain nitrogen atoms, such as some blister agents, nerve agents, and incapacitating agents.

The identification of certain compounds from other similar compounds is also desirable in several household and industrial applications. For example, a chemical sensor can indicate an excessive amount of carbon monoxide. The presence or absence of a particular chemical can also be used to control some industrial processes. Detecting particular contaminants or byproducts is also useful for quality control purposes.

It would be desirable to use the low-cost possibilities of OTFTs to perform some of the chemical sensing functions mentioned above.

BRIEF DESCRIPTION

The present disclosure relates, in several embodiments, to electronic devices that are useful for detecting, identifying, and/or quantifying certain compounds, either specifically or by general class or shared chemistry. The electronic devices include a chemically sensitive transistor that produces different signals, such as changes in charge carrier mobility, when exposed to different chemical compounds. The devices include a first transistor and optionally a second or further transistors whose response to a given compound, such as a volatile substance, differs. The response differs both from a baseline for the transistor and changes independently of the response of other transistors. This differing response can be used to detect, identify, and/or quantify the compound.

Disclosed in some embodiments herein is system for detecting and/or determining the identity of a chemical compound, such as the vapors of nitrogen-containing explosive compounds. The system includes an electronic device and an analyzer. The electronic device comprises at least a first chemically sensitive thin film transistor. The first transistor produces a change in charge carrier mobility when exposed to different chemical compounds. As a result, the change can be used to detect and/or identify the chemical compound. A scanner, reader, or analyzer is used in conjunction to obtain information from the electronic device, particularly to determine the identity of the chemical compound.

More particularly, the chemical compound which the device is used to detect or identify is selected from the group consisting of hydrocarbons containing one or more nitro groups, chlorinated hydrocarbons, alcohols, and aromatic hydrocarbons.

In specific embodiments, the first transistor comprises a first semiconducting layer, the first semiconducting layer comprising a first semiconductor and carbon nanotubes.

In further embodiments, the electronic device further comprises a second transistor. The second transistor comprises a second semiconducting layer, wherein the second semiconducting layer comprises a second semiconductor and does not contain carbon nanotubes. The difference in the composition of the first and second semiconducting layers causes each transistor to produce a different change in charge carrier mobility compared to each other when exposed to the same chemical compound. Each transistor also responds differently to different chemical compounds. The combination of differing responses between the two transistors can be used to further discriminate between chemical compounds and/or serve to confirm the identity of the chemical compound produced by one of the transistors alone.

It is contemplated that the electronic device can be made in the form of a cartridge which can be read by the complementary analyzer. The cartridge can then be disposed of. The analyzer is used to process the information generated by the electronic device. For example, the analyzer may contain a reference lookup table for various values generated by the electronic device, a data processing system, etc.

Disclosed in some embodiments is an electronic device for determining the specific identity of a chemical compound. The electronic device comprises a first transistor and a second transistor. The first transistor comprises a first semiconducting layer, the first semiconducting layer comprising a first semiconductor and carbon nanotubes. The second transistor comprises a second semiconducting layer, wherein the second semiconducting layer comprises a second semiconductor and does not contain carbon nanotubes. Each transistor has a unique response, such as a change in charge carrier mobility, to different chemical compounds and/or chemical compositions. This is used to determine the specific identity of the chemical compound.

The first semiconductor and the second semiconductor can each be a polythiophene. In embodiments, the first semiconductor and the second semiconductor independently have a structure of Formula (I):

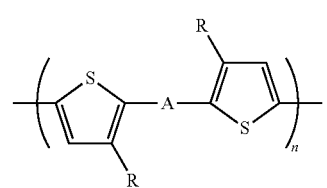

Formula (I)

wherein A is a divalent linkage; wherein each R is independently selected from hydrogen, alkyl, substituted alkyl, alkenyl, substituted alkenyl, alkynyl, substituted alkynyl, aryl, substituted aryl, alkoxy, substituted alkoxy, a heteroatom-containing group, halogen, —CN, or —NO₂; and wherein n is from 2 to about 5,000.

In specific embodiments, each R is alkyl having from about 6 to about 25 carbon atoms.

In other embodiments, the first semiconductor and the second semiconductor each have the structure of Formula (II):

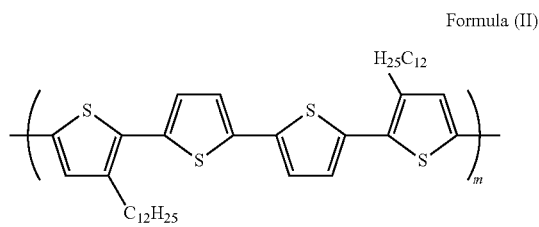

Formula (II)

wherein m is from 2 to about 2,500.

The carbon nanotubes in the first semiconducting layer can be single-wall carbon nanotubes or surface-modified carbon nanotubes. The carbon nanotubes may comprise from about 1 wt % to about 50 wt % of the first semiconducting layer, based on the total weight of the first semiconductor and the carbon nanotubes.

Also disclosed is an electronic device comprising a first transistor and a second transistor. The first transistor comprises a first gate electrode, a first source electrode, a first drain electrode, and a first semiconducting layer, the first semiconducting layer comprising a first semiconductor polythiophene and carbon nanotubes. The second transistor comprises a second gate electrode, a second source electrode, a second drain electrode, and a second semiconducting layer, wherein the second semiconducting layer comprises a second semiconductor polythiophene and does not contain carbon nanotubes. The first transistor and the second transistor share a common substrate and a common dielectric layer separating the first gate electrode and the second gate electrode from the first source electrode, the first drain electrode, the second source electrode, and the second drain electrode. In particular embodiments, the first semiconductor polythiophene and second semiconductor polythiophene can independently have the structure of Formulas (I) or (II).

Also disclosed herein is a method for detecting a chemical compound, or more particularly an explosive compound. An electronic device is received that comprises at least a first transistor, the first transistor comprising a first semiconducting layer. The electronic device is exposed to a vapor stream. The response of the electronic device is examined using an analyzer to determine the presence of a compound in the vapor stream that indicates the presence of an chemical compound. This can include identifying the chemical compound in the vapor stream.

More specifically, examining the response includes comparing the change in charge carrier mobility of the first transistor when exposed to the vapor stream against the response when not exposed to the vapor stream (i.e. exposed to ambient conditions) to determine the presence of the compound in the vapor stream.

In particular embodiments, the electronic device contains a first transistor and a second transistor. The first semiconducting layer comprises a first semiconductor and carbon nanotubes. The second transistor comprises a second semiconducting layer, wherein the second semiconducting layer comprises a second semiconductor and does not contain carbon nanotubes. The different changes in charge carrier mobility of the first transistor and the second transistor are compared to determine the presence of the compound in the vapor stream. In particular embodiments, the first semiconductor and second semiconductor can independently have the structure of Formulas (I) or (II).

Also disclosed herein is a method for detecting explosive compounds. An electronic device is received that comprises a first transistor and a second transistor. The first transistor comprises a first semiconducting layer, the first semiconducting layer comprising a first semiconductor and carbon nanotubes. The second transistor comprises a second semiconducting layer, wherein the second semiconducting layer comprises a second semiconductor and does not contain carbon nanotubes. The electronic device is exposed to a vapor stream. The differing response between the first transistor and the second transistor is examined to detect the presence of compounds in the vapor stream that indicate the presence of explosive compounds.

The differing response may be seen in the charge carrier mobility of the first transistor and the second transistor.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
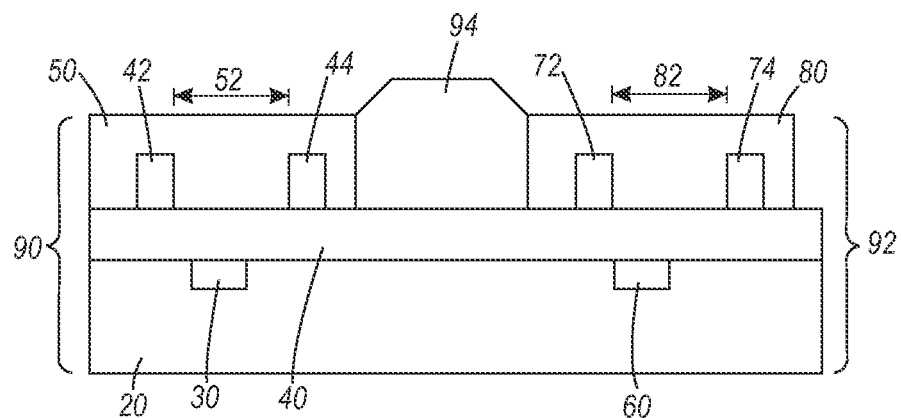
FIG. 1 is a diagram of a first embodiment of a TFT according to the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of from about 2 to about 10" also discloses the range "from 2 to 10."

The term "comprising" is used herein as requiring the presence of the named component and allowing the presence of other components. The term "comprising" should be construed to include the term "consisting of", which allows the presence of only the named component, along with any impurities that might result from the manufacture of the named component.

The term "room temperature" refers to a temperature in the range of 20° C. to 25° C.

Generally, the present disclosure relates to electronic devices which can be used as chemical sensors. The charge carrier mobility of the (or each) transistor on the electronic device is measured when exposed to ambient air, and this measurement is used as a baseline. When the electronic device is then exposed to a vapor stream containing a particular chemical compound, the change in the charge carrier mobility (absolute change, relative change, or both) can be used to identify the particular chemical compound. A particular transistor generally has a different response when exposed to different chemical compounds. This can allow the chemical compound to be identified either generally (e.g. falling within a certain class or containing certain chemical constituents) or specifically. Different transistors can respond independently. This differing response between different transistors provides independent confirmation of the presence or identity of the chemical compound. The electronic devices are particularly useful for determining the general class, composition, and/or identity of a chemical compound in a vapor stream.

It is particularly contemplated that the electronic device is used as a chip or cartridge in conjunction with a scanner, reader, or similar analyzer that interprets the information generated by the electronic device. For example, the analyzer can be used to read, process, interpret, or obtain data concerning the vapor stream, and to generate an appropriate display, store the data, etc. The identification of the chemical compound can be made, for example, by comparison to a reference table that relates the change in charge carrier mobility to a class of compounds or a specific chemical compound. The cartridge can then be disposed of, if desired. In specific applications, the electronic device can be used to detect vapors of explosive compounds, decomposition fragments of explosive compounds, or vapors of chemicals commonly associated with explosive compounds.

In more specific embodiments, the electronic device includes a first transistor and a second transistor, and can include additional transistors as desired. Each transistor acts as a chemical sensor, and provides a distinct response to a given chemical compound. Generally, the response to a particular compound differs between the two (or more) transistors. These differing responses can be used to further distinguish between different chemical compounds. For example, the electronic device can selectively identify chloroform from other chlorinated solvents, or selectively detect n-butanol from other alcohol based solvents.

More particularly, the first transistor comprises a first semiconducting layer that contains a first semiconductor and carbon nanotubes. The second transistor comprises a second semiconducting layer that contains a second semiconductor, but does not contain carbon nanotubes. Processes for making such an electronic device are also disclosed. Methods for using the electronic device are also disclosed.

FIG. 1 illustrates an electrical device having at least a first transistor and using a bottom-gate bottom-contact TFT configuration. The electronic device 10 comprises a substrate 20 that serves as a lowest or bottommost layer, and can be considered to be one of the outermost layers of the transistor(s). A first gate electrode 30 is located within the substrate, and a gate dielectric layer 40 covers the first gate electrode. The first gate electrode 30 is depicted here in a depression within the substrate 20, but the gate electrode could also be located atop the substrate (i.e. in a depression within the gate dielectric layer). It is important that the gate dielectric layer 40 separates the first gate electrode 30 from the first source electrode 42, first drain electrode 44, and the first semiconducting layer 50. The first semiconducting layer 50 runs over and between the first source and drain electrodes 42 and 44. The first semiconducting layer has a channel length 52 between the first source and drain electrodes 42 and 44. The substrate 20, first gate electrode 30, gate dielectric layer 40, first source electrode 42, first drain electrode 44, and first semiconducting layer 50 together may be considered as forming a first transistor 90.

A second gate electrode 60 is also located within the substrate, with the gate dielectric layer 40 covering the second gate electrode. Again, the second gate electrode 60 is depicted here in a depression within the substrate 20, but the gate electrode could also be located atop the substrate (i.e. in a depression within the gate dielectric layer). Again, the gate dielectric layer 40 separates the second gate electrode 60 from the second source electrode 72, second drain electrode 74, and the second semiconducting layer 80. The second semiconducting layer 80 runs over and between the second source and drain electrodes 72 and 74. The second semiconducting layer has a channel length 82 between the second source and drain electrodes 72 and 74. The substrate 20, second gate electrode 60, gate dielectric layer 40, second source electrode 72, second drain electrode 74, and second semiconducting layer 80 together may be considered as forming a second transistor 92. It should be noted that here, the substrate 20 and the gate dielectric layer 40 are shared in common between the two transistors.

It is also contemplated that the two transistors could have their own substrate and gate dielectric layer. The first transistor 90 and second transistor 92 are electrically separated from each other. An insulator 94 is illustrated here as separating the two transistors. Generally, when more than one transistor is present, the transistors are electrically separated from each other.

Figure 2:
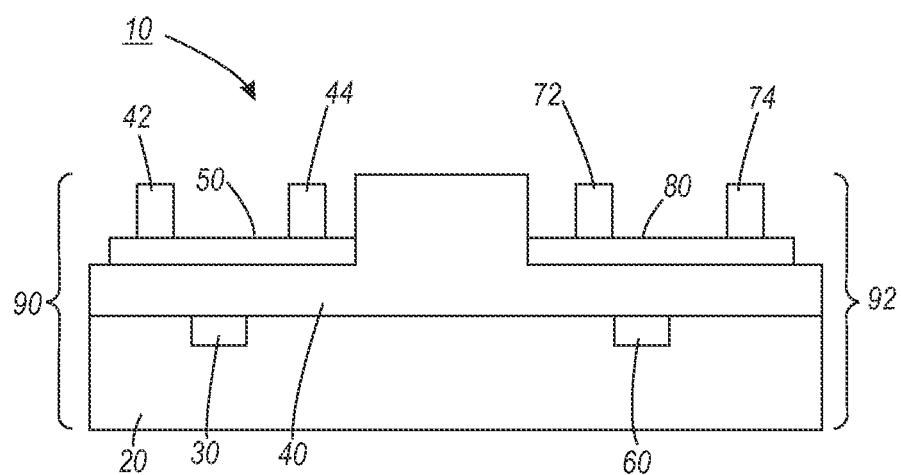
FIG. 2 is a diagram of a second embodiment of a TFT according to the present disclosure.

FIG. 2 illustrates an electronic device using a bottom-gate top-contact TFT configuration. Here, the first semiconducting layer 50 and the second semiconducting layer 80 are placed on top of the gate dielectric layer 40. The first source electrode 42 and the first drain electrode 44 are then placed on top of the first semiconducting layer 50. The second source electrode 72 and the second drain electrode 74 are then placed on top of the second semiconducting layer 80. Here, the dielectric layer 40 is shaped to form a wall that separates the two transistors.

Figure 3:
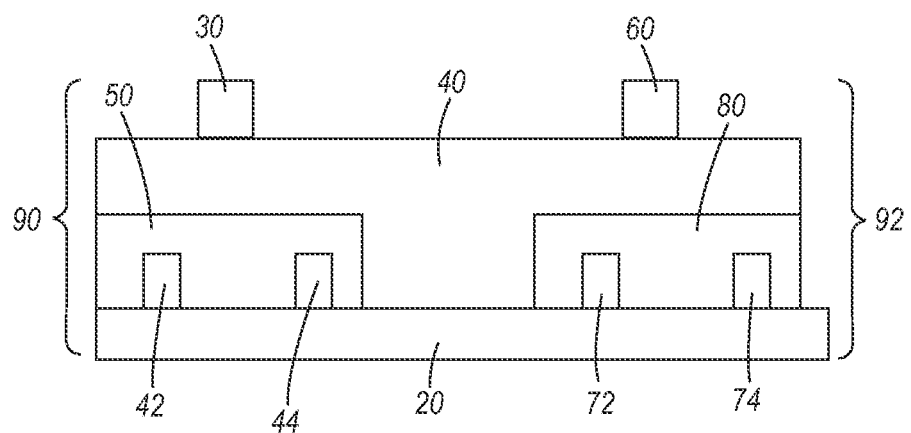
FIG. 3 is a diagram of a third embodiment of a TFT according to the present disclosure.

FIG. 3 illustrates an electronic device using a top-gate top-contact TFT configuration. Here, the substrate 20 is in contact with the first source electrode 42, the first drain electrode 44, and the first semiconducting layer 50. The first semiconducting layer 50 runs over and between the first source electrode 42 and the first drain electrode 44. The substrate 20 is also in contact with the second source electrode 72, the second drain electrode 74, and the second semiconducting layer 80. The second semiconducting layer 80 runs over and between the second source electrode 72 and the second drain electrode 74. The gate dielectric layer 40 is on top of the first semiconducting layer 50 and the second semiconducting layer 80. The first gate electrode 30 and the second gate electrode 60 are on top of the gate dielectric layer 40. Neither the first gate electrode 30 nor the second gate electrode 60 contact the first semiconducting layer 50 or the second semiconducting layer 80.

In specific embodiments, the first semiconducting layer 50 of the present disclosure comprises carbon nanotubes and a first semiconductor. The first semiconductor is a polymer which is capable of forming polymer aggregates. The term "polymer aggregates" refers to the ability of the polymer to form discrete particles or clusters of polymer molecules rather than a dissolved individual molecular chain. Such particles have a diameter of from about a few nanometers to about a few micrometers. In embodiments, the first semiconductor is a conjugated polymer, the conjugated polymer aggregates having a particle size from about 5 nanometers to about 1 micrometer, including from about 5 nanometers to about 500 nm, as determined using a light scattering method.

In embodiments, the polymer can form stable aggregates at room temperature in the liquid. A variety of processes can be used to form the polymer aggregates, including but not limited to those disclosed in, for example, U.S. Pat. No. 6,890,868 or 6,803,262, which are fully incorporated by reference herein.

In embodiments, the first semiconductor is a polythiophene having the structure of Formula (I):

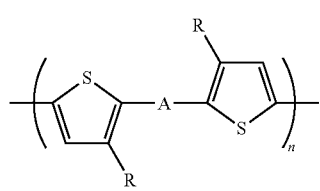

Formula (I)

wherein A is a divalent linkage; each R is independently selected from hydrogen, alkyl, substituted alkyl, alkenyl, substituted alkenyl, alkynyl, substituted alkynyl, aryl, substituted aryl, alkoxy or substituted alkoxy, a heteroatom-containing group, halogen, —CN, or —NO$_2$; and n is from 2 to about 5,000. The polythiophene of Formula (I) is a homopolymer and is capable of forming polymer aggregates.

The term "alkyl" refers to a radical composed entirely of carbon atoms and hydrogen atoms which is fully saturated. The alkyl radical may be linear, branched, or cyclic. The alkyl radical may form a single bond with only one non-hydrogen atom, or with two different non-hydrogen atoms, depending on its context. In other words, an alkyl radical has the formula —C$_n$H$_{2n+1}$ or the formula —C$_n$H$_{2n}$—.

The term "alkenyl" refers to a radical composed entirely of carbon atoms and hydrogen atoms which contains at least one carbon-carbon double bond that is not part of an aryl or heteroaryl structure. The alkenyl radical may be linear, branched, or cyclic.

The term "alkynyl" refers to a radical composed entirely of carbon atoms and hydrogen atoms which contains at least one carbon-carbon triple bond.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms). The aryl radical may form a single bond with only one non-hydrogen atom, or with two different non-hydrogen atoms, depending on its context. Exemplary aryl groups include phenyl (—C$_6$H$_5$), biphenyl, fluorenyl, and phenylene (—C$_6$H$_4$—).

The term "alkoxy" refers to an alkyl radical which is attached to an oxygen atom, i.e. -O—C$_n$H$_{2n+1}$.

The term "heteroatom-containing group" refers to a cyclic radical containing at least one heteroatom in a ring of the cyclic radical. The cyclic radical may be aromatic or non-aromatic. The heteroatom is generally nitrogen, oxygen, or sulfur. Exemplary heteroatom-containing groups include pyrrolidinyl, pyrryl, furyl, piperidinyl, and pyridinyl. Aromatic heteroatom-containing groups may also be specifically referred to herein as heteroaryl.

The term "substituted" refers to at least one hydrogen atom on the named radical being substituted with another functional group, such as halogen, —CN, —NO$_2$, —COOH, or —SO$_3$H. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an aryl or heteroatom-containing group may also be substituted with alkyl or alkoxy. Exemplary substituted aryl groups include methylphenyl and methoxyphenyl.

Generally, the alkyl, alkenyl, alkynyl, and alkoxy groups each independently contain from 1 to 30 carbon atoms, but in particular embodiments may have from 2 to 10 carbon atoms. Similarly, the aryl groups independently contain from 6 to 30 carbon atoms. In embodiments, n is from about 5 to about 5,000.

The term "divalent linkage" refers to any moiety which is able to form a single bond with two different non-hydrogen atoms, joining those two different atoms together. Exemplary divalent linkages include —O—, —NH—, alkyl, and aryl.

The divalent linkage A forms a single bond to each of the two thienyl moieties in Formula (I). Exemplary divalent linkages A include:

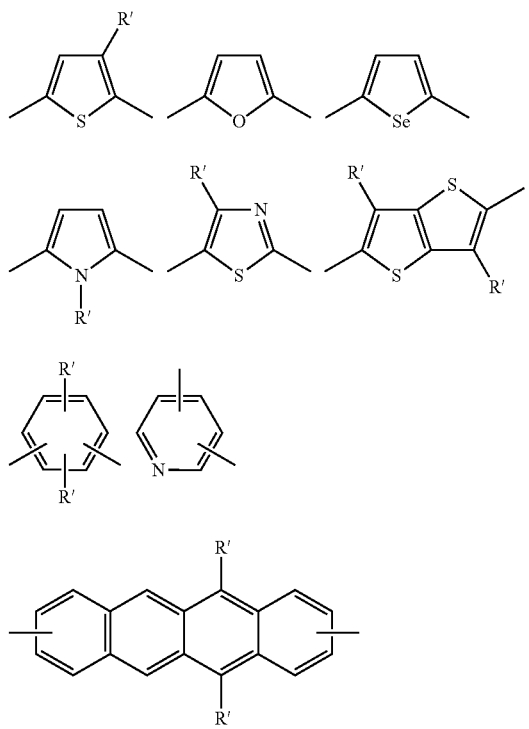

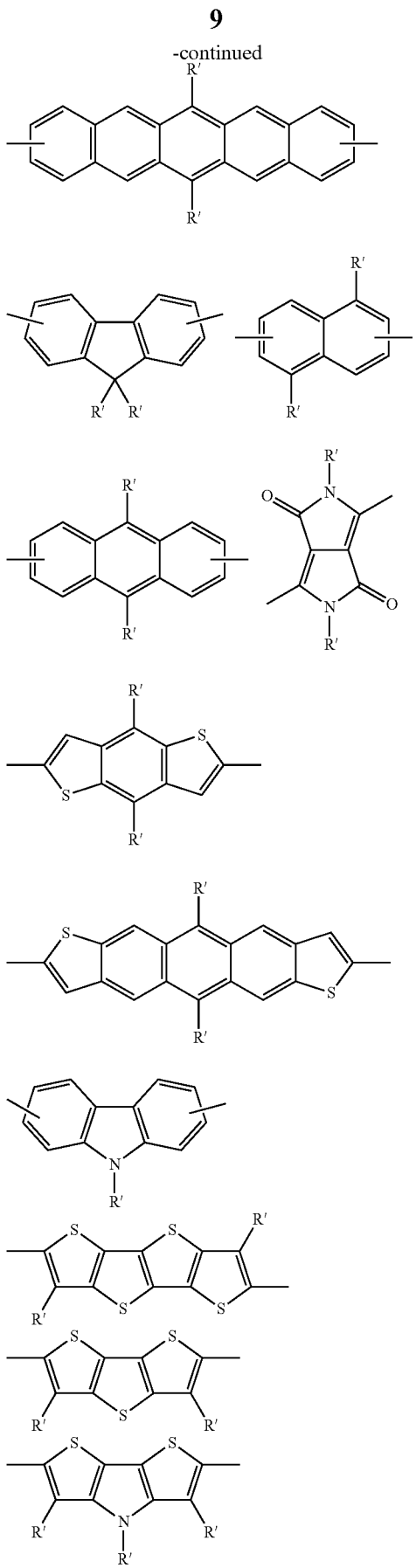

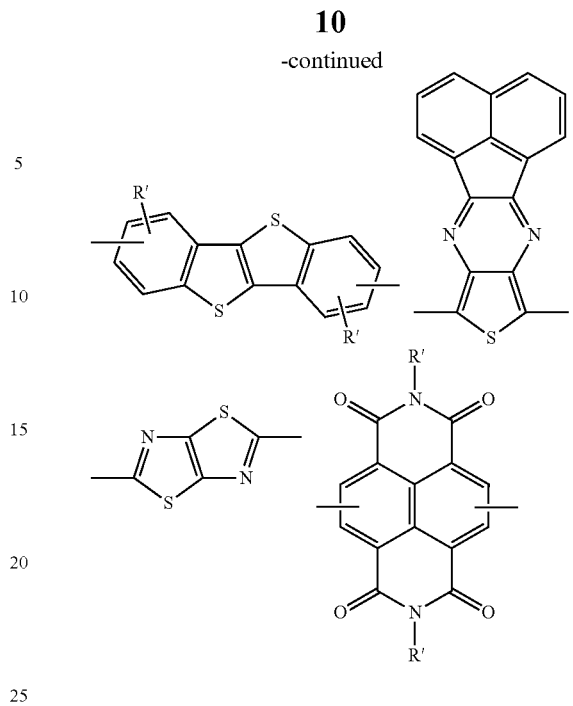

and combinations thereof, wherein each R' is independently selected from hydrogen, alkyl, substituted alkyl, aryl, substituted aryl, alkoxy or substituted alkoxy, a heteroatom-containing group, halogen, —CN, or —NO$_2$. One or more of these moieties may be present in divalent linkage A. In addition, one or more of a particular moiety may be present in divalent linkage A.

It should be noted that the divalent linkage A will always be different from the two thiophene monomers shown in Formula (I); in other words, Formula (I) will not reduce to being a polythiophene made from only one moiety. In particular embodiments, A can be a thienyl moiety which is different from that of the two thiophene moieties shown in Formula (I). For example, R and R' are not the same when A is a thienyl moiety.

In specific embodiments of Formula (I), R is alkyl having from about 6 to about 25 carbon atoms, or R is alkyl having from about 8 to about 16 carbon atoms.

In some specific embodiments, the first semiconductor is a polythiophene having the structure of Formula (II):

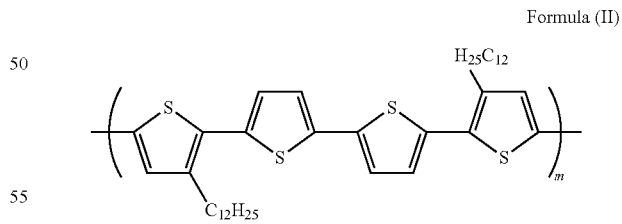

Formula (II)

wherein m is from 2 to about 2,500. The polythiophene may be referred to as PQT-12.

The first semiconducting layer also comprises carbon nanotubes. Carbon nanotubes are an allotrope of carbon. They take the form of cylindrical carbon molecules and have novel properties that make them useful in a wide variety of applications in nanotechnology, electronics, optics, and other fields of meterials science. Carbon nanotubes exhibit extraordinary strength, unique electrical properties, and efficient heat conductor properties. The diameter of a nanotube is small, typically on the order of a few nanometers. The length of a nanotube is typically larger, sometimes up to several millimeters. In other words, the carbon nanotubes may have a high aspect ratio, i.e. ratio of length to diameter.

The carbon nanotubes may be single-wall carbon nanotubes, double-wall carbon nanotubes, or multi-wall carbon nanotubes. A single-wall carbon nanotube is a cylinder in which each carbon atom is joined to four other carbon atoms, similar (but not identical to) to the bonds in a rectangular graphene sheet. A multi-wall carbon nanotube is composed of a number of cylindrical carbon nanotubes having different diameters, which are formed concentrically around each other. The carbon nanotubes can have any suitable length and diameter.

In embodiments, the carbon nanotubes are single-wall carbon nanotubes (SWCNTs). The SWCNTs have a diameter from about 0.5 nanometers to about 2.5 nanometers, including from about 0.7 to about 2.5 nm. In some specific embodiments, the SWCNTs may have a diameter from about 0.7 to 1.2 nm, or from about 0.7 to about 1.0 nm. The SWCNTs may have a length from about 0.1 to about 10 micrometers, including from about 0.5 to about 5 micrometers, from about 0.5 to about 2.5 micrometers, or from about 0.7 to about 1.5 micrometers. The aspect ratio of the SWCNTs may be from about 500 to about 10,000, including from about 500 to 5,000, or from 500 to 1500. These sentences should not be construed as requiring that all nanotubes have the same diameter, length, or aspect ratio. Rather, the nanotubes may have differing diameters, lengths, or aspect ratios within the listed distribution ranges. In specific embodiments, the carbon nanotubes are single-wall semiconducting carbon nanotubes.

In other embodiments, the carbon nanotubes may be surface-modified carbon nanotubes. The surface-modifying group can be attached on the wall or at the ends of the carbon nanotubes. The surfaces of the carbon nanotubes can be modified in two ways: non-covalent attachment and covalent attachment.

In embodiments, the surface-modified carbon nanotubes may be represented by the following formula:

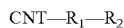

wherein CNT represents the carbon nanotube, $R_1$ is a linking group selected from ester (—COO—) and amide (—CONH—); and $R_2$ is a conjugated group, a non-conjugated group, a small molecular group, an inorganic material, and combinations thereof. The degree of surface modification may vary from about one group per carbon nanotube to about one thousand groups per carbon nanotube.

The surfaces of the carbon nanotubes may be modified with a conjugated group, a non-conjugated group, an inorganic material, and combinations thereof.

Exemplary conjugated groups may include thiophene-based oligomers, pyrenyl, fluorenyl, carbazolyl, triarylamine, and phenyl. The conjugated group can be covalently bonded directly to the surface of the carbon nanotubes or through a linking group, such as amide or ester.

Exemplary non-conjugated groups may include alkyl, alkoxy, cyano, nitro, urethane, styrene, acrylate, amide, imide, ester, and siloxanes. Also included are non-conjugated groups comprising an acidic moiety, selected from the group consisting of carboxylic acid, sulfonic acid, phosphinic acid, sulfuric acid, nitric acid, phosphoric acid, and the like. In specific embodiments, the surface-modified carbon nanotubes are modified with carboxylic acid, sulfuric acid, and nitric acid. The carbon nanotube-supported acid can dope a semiconductor, particularly p-type semiconductor, to enhance conductivity of the semiconductor layer and thus the field-effect mobility of the transistors.

In specific embodiments, the inorganic material may be conducting or semiconducting. Exemplary inorganic materials include metals and metal oxides such as gold, silver, copper, nickel, zinc, cadmium, palladium, platinum, chromium, aluminum, ZnO, ZnSe, CdSe, $Zn_aIn_bO_c$ (where a, b, and c are integers), GaAs, $ZnO.SnO_2$, $SnO_2$, gallium, germanium, tin, indium, indium oxide, indium tin oxide, and the like. The inorganic material may homogenously cover the surface of the carbon nanotubes or be in nanoparticle form on the surface of the carbon nanotubes. In specific embodiment, the surface-modified carbon nanotubes are modified with nanoparticles selected from the group consisting of gold, silver, nickel, copper, ZnO, CdSe, $Zn_aIn_bO_c$, GaAs, $ZnO.SnO_2$, $SnO_2$, and ZnSe nanoparticles.

Modifying the surface of the carbon nanotubes can enable better miscibility between the carbon nanotubes and the polythiophene of Formula (I). Typically, nanoparticles prefer to form aggregates, due to strong van der Waals force, so that nano-scale dispersion is difficult to achieve. The surface modification increases solubility and allows real nano-scale dispersion of the carbon nanotubes in the polythiophene. When the surface is modified with a conjugated moiety, better charge transfer occurs between the carbon nanotubes and the polythiophene semiconductor.

Carbon nanotubes can be surface modified by suitable methods. For example, a reactive site can be created on the carbon nanotubes, then an oligomer or small molecular compound can be grafted onto the nanotubes at that reactive site. Another approach involves the introduction of carboxylic acid groups onto a carbon nanotube surface via an acid treatment. For example, a mixture of sulfuric acid and nitric acid can be used to form carboxylic acid groups on the surface of a carbon nanotube. Other surface modifying groups can then react with the carboxylic acid group. Other approaches include plasma treatment or direct reaction with highly reactive chemicals such as dichlorocarbene. In other embodiments, the carbon nanotubes are not surface modified.

The first semiconductor can stabilize the carbon nanotubes in a semiconducting composition containing a solvent. This stabilization can occur through several different mechanisms. In embodiments, the property of being capable of forming polymer aggregates helps to disperse and stabilize the carbon nanotubes in the semiconductor composition. As a result, the polymer aggregates help to disperse and stabilize the carbon nanotubes in the solvent. In other embodiments, the dispersed carbon nanotubes function as nuclei, with the first semiconductor wrapping around the individual carbon nanotubes to form a nano aggregate of the carbon nanotubes and the first semiconductor. These nano aggregates may co-exist together with the polymer aggregates. The presence of semiconductor wrapped carbon nanotubes and/or semiconducting polymer aggregates can be examined using suitable tools such as high resolution transmission electron microscopy or atomic force microscopy techniques.

The first semiconducting layer 50 may comprise from about 1 wt % to about 50 wt % carbon nanotubes, based on the total weight of the first semiconductor and the carbon nanotubes. In some embodiments, the carbon nanotubes comprise from about 3 to about 40 wt % of the first semiconducting layer.

The weight ratio of carbon nanotubes to first semiconductor in the first semiconducting layer may be from about 1:99 to about 50:50. In some embodiments, the weight ratio of carbon nanotubes to polythiophene in the first semiconducting layer is from about 5:95 to about 40:60.

In some specific embodiments where the electronic device includes a second transistor, the second semiconducting layer 80 of the second transistor comprises a second semiconductor, and does not include carbon nanotubes. Exemplary semiconductors include but are not limited to acenes, such as anthracene, tetracene, pentacene, rubrene, and substituted pentacenes such as TIPS-pentacene; perylenes, fullerenes, oligothiophenes, polythiophenes and their substituted derivatives, polypyrrole, poly-p-phenylenes, poly-p-phenylvinylidenes, naphthalenedicarboxylic dianhydrides, naphthalene-bisimides, polynaphthalenes, phthalocyanines such as copper phthalocyanines, titanyl phthalocyanines, or zinc phthalocyanines and their substituted derivatives, and other fused ring structures such as substituted benzothieno[3,2-b]benzothiophene, triethylsilylethynyl anthradithiophene, and the like.

In particular embodiments, the second semiconductor is a polythiophene. In more specific embodiments, the second semiconductor is a polythiophene that also has the structure of Formula (I) or Formula (II), as described above. The polythiophene in the second semiconducting layer 80 of the second transistor may be the same or a different polythiophene as the polythiophene in the first semiconducting layer 50 of the first transistor. The second semiconducting layer 80 is free or substantially free of carbon nanotubes. In some embodiments, the polythiophene of both the first semiconducting layer 50 and the second semiconducting layer 80 is PQT-12 as illustrated in Formula (II).

The first semiconducting layer containing a first semiconductor and carbon nanotubes is generally formed by solution deposition. In this regard, it has been found that to achieve both good dispersion of the carbon nanotubes in the first semiconductor (such as polythiophene), a two-step process must be used. Generally speaking, carbon nanotubes and a first amount of the first semiconductor are dispersed in a liquid to form a first dispersion. A second amount of the first semiconductor is then added to the first dispersion to form a loaded dispersion. The second amount of the first semiconductor is then dissolved or dispersed in the loaded dispersion to form a final dispersion.

Put another way, the carbon nanotubes are dispersed in a first amount of the polythiophene in a solvent to form a first dispersion. The carbon nanotubes are stabilized by the polythiophene. Next, a second amount of the polythiophene is added to the first dispersion to form a loaded dispersion. The second amount of the polythiophene is then dispersed in the loaded dispersion to form a final dispersion. In embodiments, the polythiophene is capable of forming polymer aggregates in the liquid.

A mixture of solvent, first semiconductor (which is a polymer), and carbon nanotubes is usually heated to a first elevated temperature to at least partially dissolve the first semiconductor. The warm mixture is then lowered to a first lower temperature and probe-sonicated to form the first dispersion. The sonication can be conducted prior to, during, or after lowering the temperature to the first lower temperature. While lowering the temperature, the first semiconducting polymer forms polymer aggregates at the first lower temperature, and the carbon nanotubes are dispersed and stabilized with the first semiconducting polymer and the polymer aggregates. The carbon nanotubes can be dispersed very well in a polythiophene solution and at a very high loading, i.e. close to a 1:1 weight ratio. The second amount of the first semiconductor is then added to the first dispersion to form a loaded dispersion. The loaded dispersion is optionally heated to a second elevated temperature, where the second amount of the first semiconductor is at least partially dissolved in the liquid at the second elevated temperature. The loaded dispersion is lowered to a second lower temperature (which is lower than the second elevated temperature) and bath sonicated to form the final dispersion. In some embodiments, the first elevated temperature is the same as the second elevated temperature. In other embodiments, the first elevated temperature is higher than the second elevated temperature by 5 to about 100 degree C., including 10 to about 50 degree C. In some embodiments, the first lower temperature is below room temperature, and the second lower temperature is room temperature. In other embodiments, both the first and the second lower temperatures are below room temperature. After being lowered to the second lower temperature, the composition is brought to room temperature.

In embodiments, the first dispersion is formed by using a probe sonication, and the final dispersion is formed by using a bath sonication. The term "probe sonication" refers to sonication wherein a probe is inserted into a container containing the dispersion. The term "bath sonication" refers to sonication wherein the container containing the dispersion is placed into a bath, and the bath is subsequently sonicated. Probe sonication provides much greater energy/power compared to bath sonication. Put another way, for the two-step process, high power or high energy is used during the first dispersing step, while significantly lower energy/power is used during the second dispersing step.

The two semiconducting layers may be formed in an electronic device using conventional processes known in the art. In embodiments, the semiconducting layers are formed using solution depositing techniques. Exemplary solution depositing techniques include spin coating, blade coating, rod coating, dip coating, screen printing, ink jet printing, stamping, stencil printing, screen printing, gravure printing, flexography printing, and the like. Alternatively, the semiconducting layers may be vapor deposited.

Each semiconducting layer can be from about 5 nanometers to about 1000 nanometers deep, including from about 20 to about 100 nanometers in depth. In certain configurations, such as the configuration shown in FIG. 1, the semiconducting layer completely covers its respective source and drain electrodes.

A thin film transistor generally includes a substrate, an optional gate electrode, source electrode, drain electrode, and a dielectric layer in addition to the semiconducting layer. As previously discussed above, the two transistors in the electronic device of the present disclosure can share a substrate and dielectric layer in common.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

In the present disclosure, the dielectric layer may be surface modified with a surface modifier. The two semiconducting layers can be directly contacted with this modified dielectric layer surface. The contact may be complete or partial. This surface modification can also be considered as forming an interfacial layer between the dielectric layer and the semiconducting layer. In particular embodiments, the surface of the dielectric layer has been modified with an organosilane agent of Formula (A):

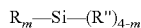  Formula (A)

wherein R is hydrocarbon or fluorocarbon containing from 1 to about 20 carbon atoms, R'' is halogen or alkoxy; and m is an integer from 1 to 4. Exemplary organosilanes include octyltrichlorosilane (OTS-8) (R=octyl, R''=chloro, m=1), dodecyltrichlorosilane, phenyltrichlorosilane, methyltrimethoxylsilane, phenylmethyldimethoxysilane, phenylmethyldichlorosilane, (3-phenylpropyl)dimethylchlorosilane, (3-phenylpropyl)methyldichlorosilane, phenyltrimethoxysilane, phenethyltrichlorosilane, and the like. In specific embodiments, the R comprises a phenyl group. Other surface modifiers such as polystyrene, polysiloxane, polysilsesquioxane can be used as well.

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

Each source electrode is grounded and a bias voltage of, for example, about 0 volt to about 80 volts is applied to the respective drain electrode to collect the charge carriers transported across the semiconductor channel when a voltage of, for example, about +10 volts to about −80 volts is applied to the appropriate gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of each OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconducting layer are on the substrate, even though one layer is closer to the substrate than the other layer. The resulting TFT has good mobility and good current on/off ratio.

Generally speaking, the transistor(s) on the electronic device is used as a chemical sensor. The charge carrier mobility of the (or each) transistor is measured when exposed to ambient air, and this measurement is used as a baseline. When the electronic device is then exposed to a vapor stream containing a particular chemical compound, the change in the charge carrier mobility (absolute change, relative change, or both) can be used to identify the particular chemical compound. A particular transistor generally has a different response when exposed to different chemical compounds. This can allow the chemical compound to be identified either generally (e.g. falling within a certain class or containing certain chemical constituents) or specifically. The identification can be made by comparison to a reference table that relates the change in charge carrier mobility to a class of compounds or a specific chemical compound.

When the first and second transistors on the electronic device are used, each transistor responds independently to a given chemical compound in the vapor stream. This differing response between the two (or more) transistors provides independent confirmation of the presence or identity of the chemical compound. In particular, it is contemplated that explosive compounds could be identified, or compounds that might suggest the presence of an explosive compound. Generally, the resulting charge carrier mobility of the first transistor and the second transistor in the presence of a chemical compound is examined to identify the compound.

More specifically, it is contemplated that the electronic device containing the first transistor and the second transistor is made in the form of a cartridge which can be exposed to the vapor stream. The cartridge is then used in conjunction with a handheld scanner/reader to read, process, interpret, or obtain data concerning the vapor stream, and to generate an appropriate display, store the data, etc. The cartridge can then be disposed of, if desired.

One method for detecting an explosive compound disclosed herein includes receiving an electronic device. The electronic device comprises at least a first transistor, the first transistor comprising a first semiconducting layer. The electronic device is exposed to a vapor stream. The response of the electronic device is then examined to determine the presence of a compound in the vapor stream that indicates the presence of an explosive compound. The electronic device here can be a chip which is initially exposed to the vapor stream and then inserted into a scanner/reader. Alternatively, the chip is inserted into the scanner/reader and then exposed to the vapor stream. The chip can be used to determine the presence or absence of any particular compound in the vapor stream that can indicate the presence of an explosive compound. For example, the particular compound in the vapor stream that is detected by the chip could be the explosive compound itself, a decomposition fragment, a solvent used in the manufacture of the explosive compound, or some other indicator. It should be noted that a single transistor can be used to detect multiple different chemical compounds, not just one specific compound. For example, a change in the charge carrier mobility of 10% might indicate compound A is present, while a change of 20% might indicate compound B is present.

The following examples are for purposes of further illustrating the present disclosure. The examples are merely illustrative and are not intended to limit devices made in accordance with the disclosure to the materials, conditions, or process parameters set forth therein. All parts are percentages by volume unless otherwise indicated.

EXAMPLES

Example 1

Single-wall carbon nanotubes (CNT) were added to 1,2-dichlorobenzene to a concentration of 0.1 wt %. The mixture was probe ultra-sonicated at 50% power for 20 seconds. PQT-12 powder was added to the CNT dispersion until a concentration of 0.1 wt % PQT-12 was attained. The weight ratio of CNT to PQT-12 was 1:1. The mixture was warmed to dissolve the PQT-12 and then probe ultra-sonicated for 20 seconds. The resultant dispersion of CNT in PQT nanoparticles was very stable. This PQT/CNT dispersion was centrifuged at 3,500 rpm for 30 minutes to remove any agglomerates.

A second PQT-containing dispersion was made containing 0.5 wt % PQT-12 in 1,2-dichlorobenzene. The PQT/CNT dispersion and the PQT-containing dispersion were mixed in an appropriate ratio to obtain a final mixture having a CNT to PQT weight ratio of 5%. This mixture was then bath sonicated to form a stable composition.

Example 2

TFTs were fabricated on a silicon wafer substrate using the PQT-12/CNT composition of Example 1 to form a semiconducting layer. N-doped silicon functioned as the gate and a 200 nm silicon oxide layer functioned as the gate dielectric. The silicon oxide was modified with octyltrichlorosilane. The PQT-12/CNT composition was spin coated on the wafer at 1,000-2,000 rpm to form the semiconducting layer. The semiconducting layer was dried at 80° C. and annealed at 140° C. in a vacuum oven. Gold source and drain electrodes were evaporated upon the semiconducting layer through a shadow mask. These TFTs contained a semiconducting layer formed from PQT-12 and carbon nanotubes, and are referred to herein below as "5% CNT".

Example 3

TFTs were fabricated on a silicon wafer substrate using a dispersion of 0.3 wt % PQT-12 in 1,2-dichlorobenzene to form a semiconducting layer. N-doped silicon functioned as the gate and a 200 nm silicon oxide layer functioned as the gate dielectric. The silicon oxide was modified with octyltrichlorosilane. The PQT-12 composition was spin coated on the wafer at 1,000-2,000 rpm to form the semiconducting layer. The semiconducting layer was dried at 80° C. and annealed at 140° C. in a vacuum oven. Gold source and drain electrodes were evaporated upon the semiconducting layer through a shadow mask. These TFTs contained a semiconducting layer formed from PQT-12, and did not contain any carbon nanotubes, and are referred to herein below as "PQT".

Testing and Results

The I-V curves of the TFTs of Examples 2 and 3 were initially characterized using a Keithley SCS-4200 system to calculate charge carrier mobility.

Figure 4:
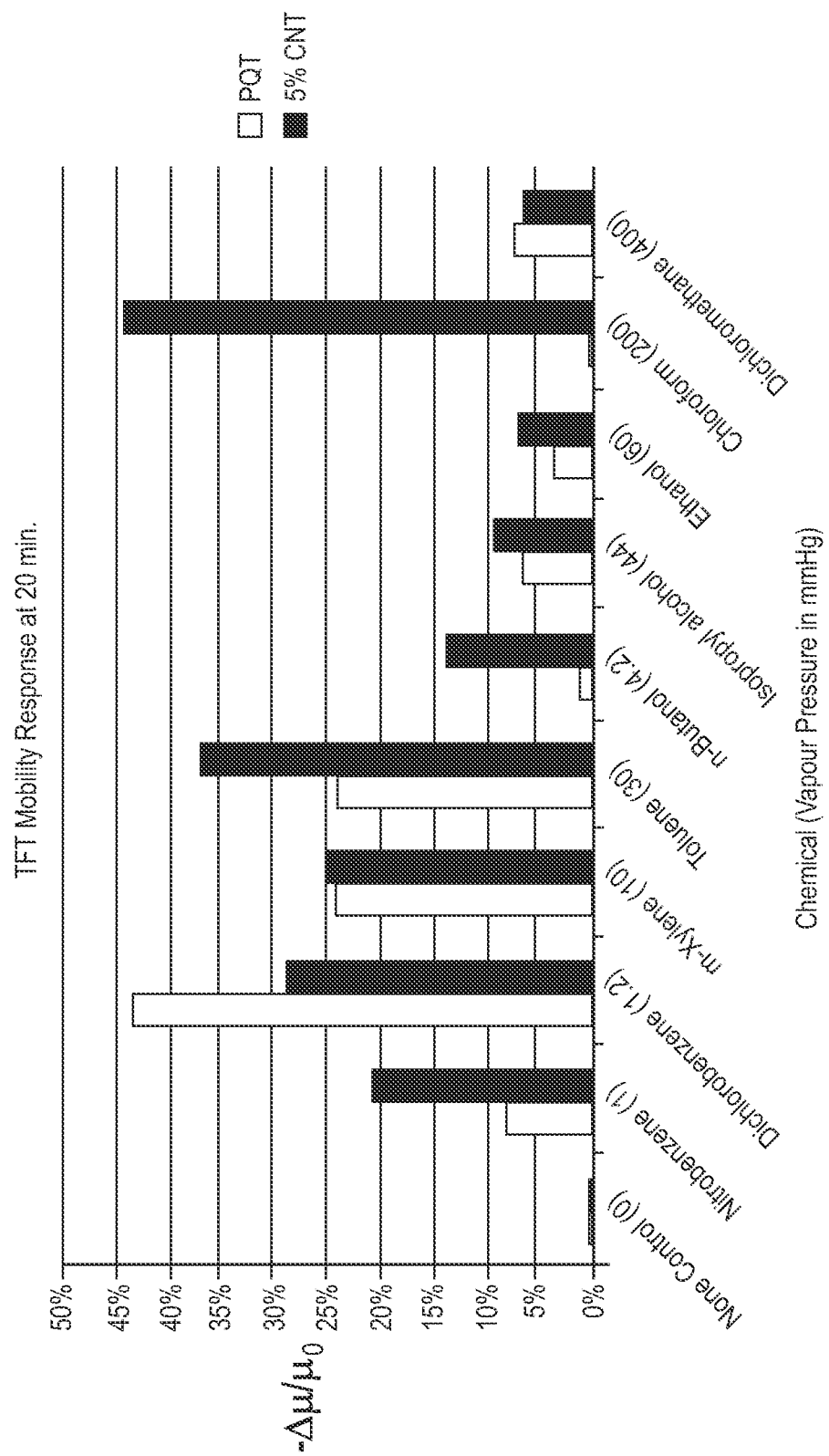
FIG. 4 is a bar graph showing the charge carrier mobility for two different TFTs for various organic solvents.

After measuring the I-V curves of the fresh devices, the TFTs of Examples 2 and 3 were exposed to a variety of organic solvents at room temperature for about 20 minutes. The devices were then evaluated again using the same measurement conditions to determine the charge carrier mobility. The change in response was determined as a percentage compared to the control. A bar graph showing the percentage change in charge carrier mobility for each TFT and each organic solvent is provided as FIG. 4.

The PQT transistors of Example 3 (with only PQT-12 in the semiconducting layer) showed good response to aromatic solvents nitrobenzene, dichlorobenzene, m-xylene, and toluene. However, they showed little or no response to alcohol-based solvents such as n-butanol, isopropyl alcohol, and ethanol. The response to chloroform was almost negligible, while the response to dichloromethane was very small.

The 5% CNT transistors of Example 2 (containing PQT-12 and carbon nanotubes in the semiconducting layer) generally showed good response to all of the solvents tested, with the lowest change for dichloromethane. They also showed higher response to n-butanol compared to the transistors of Example 3.

Table 1 below shows the % change in response for each transistor type for each solvent, as well as the ratio of PQT/5% CNT.

TABLE 1

| Solvent | PQT | 5% CNT | PQT/5% CNT |
| --- | --- | --- | --- |
| None (control) | 0 | 0 | NA |
| Nitrobenzene | 8 | 21 | 0.38 |
| Dichlorobenzene | 43 | 28 | 1.54 |
| m-xylene | 24 | 25 | 0.96 |
| Toluene | 24 | 37 | 0.65 |
| n-butanol | 1 | 14 | 0.07 |
| Isopropyl alcohol | 6 | 9.5 | 0.63 |
| Ethanol | 3 | 6.5 | 0.46 |
| Chloroform | 0 | 44 | 0.00 |
| dichloromethane | 7 | 6 | 1.17 |

The baseline measurement for both transistor types showed that the transistors were stable when not exposed to any solvents. It should be noted that the % response for the PQT transistors of Example 3 had the same % response for m-xylene and toluene. For the 5% CNT transistors of Example 2, the % response for ethanol and dichloromethane were roughly the same. However, when the % response for the two transistors were combined by using their ratio, m-xylene and toluene could be distinguished due to their different % response using the 5% CNT transistor. Similarly, ethanol and dichloromethane could be distinguished due to their different % response with the PQT transistors. The use of two transistor types served as independent confirmation of the presence of a solvent, and of the identity of that solvent.

Both transistor types showed a good percentage response to the nitrobenzene solvent. This solvent is representative of nitroaromatic compounds, which include explosive compounds such as TNT, RDX, and PETN. This means that the electronic devices of the present disclosure may be useful for the detection of such explosive compounds, and could be useful as disposable TNT sensors.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. An electronic device for determining the identity of a chemical compound, the device comprising a first transistor and a second transistor;
    wherein the first transistor comprises a first gate electrode, a first source electrode, a first drain electrode, and a first semiconducting layer, the first semiconducting layer comprising a first semiconductor polythiophene and carbon nanotubes;
    wherein the second transistor comprises a second gate electrode, a second source electrode, a second drain electrode, and a second semiconducting layer, wherein the second semiconducting layer comprises a second semiconductor polythiophene and does not contain carbon nanotubes;
    wherein the first transistor and the second transistor, when exposed to the chemical compound, produce a change in charge carrier mobility which is indicative of the chemical compound, and
    the ratio of the change in charge carrier mobility of the first transistor and the second transistor confirms the identity of the chemical compound.

2. The electronic device of claim 1, wherein the chemical compound is selected from the group consisting of hydrocarbons containing one or more nitro groups, chlorinated hydrocarbons, alcohols, and aromatic hydrocarbons.

3. The electronic device of claim 1, wherein the first semiconductor polythiophene and the second semiconductor polythiophene each have the structure of Formula (II):

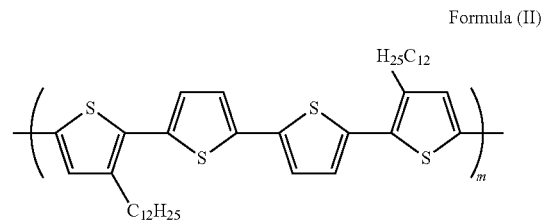

Formula (II)

wherein m is from 2 to about 2,500.

4. The electronic device of claim 1, wherein the carbon nanotubes are surface-modified carbon nanotubes.

5. The electronic device of claim 1, wherein the carbon nanotubes comprise from about 1 wt % to about 50 wt % of the first semiconducting layer, based on the total weight of the first semiconductor and the carbon nanotubes.

6. The electronic device of claim 1, wherein the first semiconductor polythiophene and the second semiconductor polythiophene independently have a structure of Formula (I):

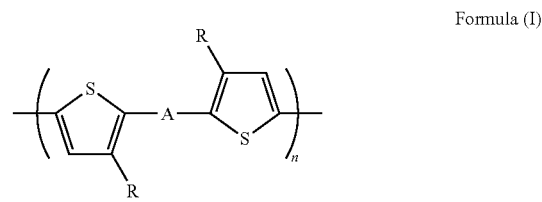

Formula (I)

wherein A is a divalent linkage; wherein each R is independently selected from hydrogen, alkyl, substituted alkyl, alkenyl, substituted alkenyl, alkynyl, substituted alkynyl, aryl, substituted aryl, alkoxy, substituted alkoxy, a heteroatom-containing group, halogen, —CN, or —NO$_2$; and wherein n is from 2 to about 5,000.

* * * * *